United States Patent [19]

Scherger

[11] Patent Number: 4,686,968

[45] Date of Patent: Aug. 18, 1987

[54] METHOD AND APPARATUS FOR RESTORING CURVATURE TO THE SPINE

[76] Inventor: John S. Scherger, 702 W. Clark, Pasco, Wash. 99301

[21] Appl. No.: 888,480

[22] Filed: Jul. 22, 1986

Related U.S. Application Data

[63] Continuation-in-part of Ser. No. 758,264, Jul. 24, 1985.

[51] Int. Cl.[4] .......... A61F 5/04

[52] U.S. Cl. .......... 128/72; 100/226; 128/33

[58] Field of Search .......... 100/226; 128/33, 63, 128/62 R, 69, 25 R, 71, 72

[56] References Cited

U.S. PATENT DOCUMENTS

| | | | |
|---|---|---|---|
| 41,548 | 2/1864 | Taylor | 128/72 |
| 978,760 | 12/1910 | Langworthy | 128/71 |
| 1,642,158 | 9/1927 | Kubista | 128/71 |
| 1,759,514 | 5/1930 | Loose . | |
| 1,953,424 | 4/1934 | Miller . | |
| 2,159,654 | 5/1939 | Catlin | 128/69 |
| 2,180,775 | 11/1939 | Steven | 128/72 |
| 2,358,254 | 9/1944 | Sanders | 128/25 |
| 2,461,102 | 2/1949 | Ackerman . | |
| 2,660,999 | 12/1953 | Thornton . | |
| 3,238,936 | 3/1966 | Siedentop | 128/71 |
| 3,550,587 | 12/1970 | Kawada . | |
| 3,640,272 | 2/1972 | Hussey . | |
| 3,904,195 | 9/1975 | Chavanne | 128/69 |
| 4,243,025 | 1/1981 | Jones | 128/70 |
| 4,466,427 | 8/1984 | Gramberg | 128/71 |
| 4,474,370 | 10/1984 | Oman | 128/69 |

*Primary Examiner*—Clyde I. Coughenour
*Attorney, Agent, or Firm*—Klarquist, Sparkman, Campbell, Leigh & Whinston

[57] ABSTRACT

A method and apparatus is disclosed for restoring curvature to the human spine. The apparatus includes a table for supporting a body in a supine position. Mounted to the table are resilient lumbar and cervical supports. The supports are each shaped to correspond substantially to their named posterior concavity of the spine for applying a static force to the concavity. A force actuator having a piston is spaced above the table to apply a force anteriorly to the spine through the body, the piston extended against and withdrawn from the body as the body resists the force through muscular action. The force actuator is longitudinally movable relative to the body in response to muscular action of the body.

8 Claims, 6 Drawing Figures

METHOD AND APPARATUS FOR RESTORING CURVATURE TO THE SPINE

This application is a continuation-in-part of U.S. application Ser. No. 06/758,264, filed July 24, 1985.

BACKGROUND OF THE INVENTION

This invention relates generally to method and apparatus for manipulating the spine and more particularly to method and apparatus for restoring curvature to a human spine.

The human spine is a column comprising thirty-three small bones or vertebrae for supporting the body. Two additional vertebrae atop the spine, the atlas and the axis, support the skull and allow it to rotate on the spine. Immediately beneath the axis are seven cervical vertebrae that make up the neck. The twelve bones immediately below them are the thoracic vertebrae of the back. These are followed by five bones that comprise the lumbar vertebrae in the small of the back. At the bottom of the spine, five bones, separate at birth, are fused during aging to form the sacrum between the hip bones. Beneath the sacrum is the coccyx, or tailbone, a single bone composed of four fused vertebrae.

The cervical and lumbar vertebrae form concave curves that alternate with a convex curve of the thoracic vertebrae to support the body and absorb shock. The resulting shape of the spine crosses the body's vertical center of gravity, weaving back and forth. The cervical curve allows the body to hold the head up without undue strain. The lumbar curve provides balance to the body and is essential for walking erect. These curves thus provide much greater stability and strength to the body than a comparable straight column could.

Loss of the spinal curves can be crippling for the body in general and the back in particular. This can occur through aging, injury, or simply poor posture. To compensate, the body responds with muscular action in an attempt to hold the head and body erect. But these muscles eventually strain, further damaging the body's health.

Recognizing this, varying methods and apparatus have been used in an attempt to manipulate the spine. U.S. Pat. No. 2,461,102 to Ackerman, for example, discloses a posture correcting apparatus employing spaced-apart rollers for rolling longitudinally along both sides of the spine. One set of rollers is mounted within a table on which the body lies, with the second set moving longitudinally along the table on top of the body.

Stretching the spine is another method employed to manipulate it. U.S. Pat. No. 2,660,999 to Thornton discloses a spinal alignment device comprising a table and a pair of opposed harnesses. One harness at the top of the table mounts to the head, and the second harness at the foot of the table mounts to the hips. The harnesses then pull in opposite directions away from each other to strengthen the spine.

A third method applies force directly to the spinal curvatures. U.S. Pat. No. 3,640,272 to Hussey illustrates this approach. A therapy table includes a cervical support shape to rest within the cervical concavity of the spine, with the body resting supinely upon the table. The body is then placed under longitudinal traction at the head and feet to align the spine.

The use of spinal supports is also employed in U.S. Pat. No. 3,550,587 to Kawada. Kawada discloses a device shaped to fit within the lumbar concavity in conjunction with a support fitting within the cervical curve of the spine. Pressure is applied to the spine solely by the weight of the body. The device then vibrates to massage the lower back.

Although these methods and associate apparatus may alleviate spinal discomfort, none has proven very effective in restoring lost spinal curvature. They and other devices in the prior art rely solely on the weight of the body as a active force. Without the exertion of muscular action to assist in holding the spine correctly, the body does not develop a "memory" of the correct spinal curvature and soon reverts to its former poor condition.

SUMMARY OF THE INVENTION

It is an object, therefore, of the present invention to provide an improved method for restoring the correct curvature to the spine.

It is also an object of the present invention to provide an apparatus for carrying out that method.

It is still another object of the invention to apply opposing forces anteriorly and posteriorly to the spine to correct the spinal curvature.

It is yet another object of the invention to exercise the muscles of the patient to aid in restoring correct spinal curvature.

To achieve these objects, an apparatus is disclosed for restoring correct curvature to the human spine. The apparatus comprises a planar surface for supporting a person's body in a supine position and a spinal support means having a shape corresponding substantially to a posterior concavity of the person's spine. The spinal support means is adapted to press against the concavity of the spine for aligning the curvature thereof. The apparatus also includes force applicator means spaced apart from the planar surface for applying a force anteriorly and normally to the spine through the supine body. The force applicator means and spinal support means thus apply simultaneous opposing forces to the spine, the forces being aligned with the spine but longitudinally offset relative to each other.

In one aspect of the invention, the spinal support means comprises a lumbar support of a shape corresponding substantially to the posterior concavity of the lumbar region. The force on the spine resulting from the lumbar support is opposed by the force applicator means which is adapted to apply a force anteriorly to the immediately adjacent thoracic region of the spine.

In another aspect of the invention, the spinal support means comprises a cervical support of a shape corresponding substantially to the posterior concavity of the cervical region. This cervical support applies a force posteriorly to the spine, which is opposed by the force applicator applying a force anteriorly to the immediate adjacent atlas region of the spine.

The force applicator means in this embodiment is a conventional linear actuator. The actuator provides a force that the body resists through muscular action as the actuator extends and withdraws.

The embodiment disclosed includes both a cervical and lumbar support mounted in combination on a table. The force applicator is spaced above the table and is longitudinally movable relative to the table and the patient's body thereon to position the applicator substantially opposite either the cervical or lumbar support. The applicator thus can selectively apply a longitudinally offset force anteriorly to the thoracic or atlas regions of the spine.

The apparatus herein illustrates a unique method for restoring correct curvature to the spine. A first force is applied uniformly to a posterior cavity of the spine. A second force is then applied simultaneously and anteriorly to the spine, the second force being aligned with the first force but longitudinally offset therefrom. The patient then resists the second force through muscular action as the second force is applied and withdrawn. In particular, the first force may be applied to the upper lumbar region simultaneously with the second force applied through the body to the adjacent thoracic region. To induce curvature in the lower lumbar region, the second force may be moved and applied through the body to the sacrum region of the spine, with the first force still in place. For inducing curvature in the cervical region, the first force may be applied to the cervical region with the second force applied through the body to the adjacent atlas region.

The foregoing and other objects, features, and advantages of the invention will become more apparent from the following detailed description of a preferred embodiment which proceeds with reference to the accompanying drawings.

DETAILED DESCRIPTION

Figure 1:
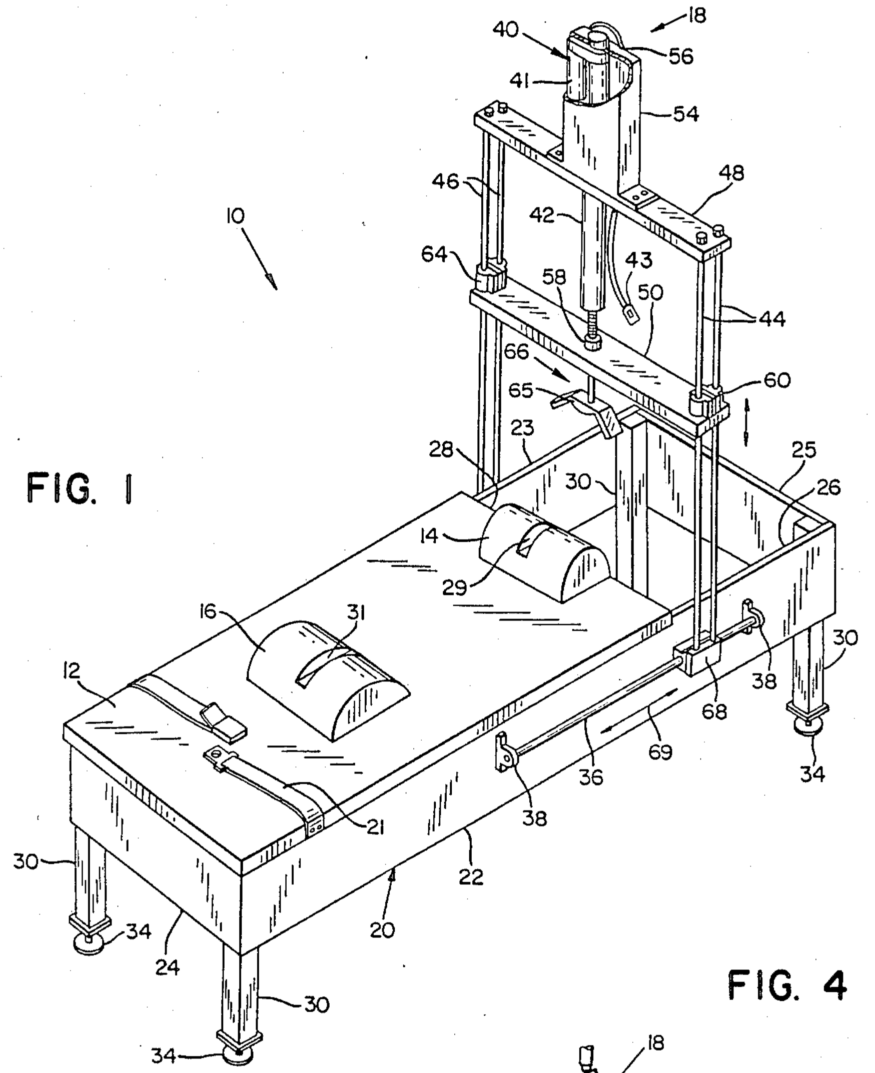
FIG. 1 is a perspective view of a spinal curvature apparatus according to the invention.
Figure 4:
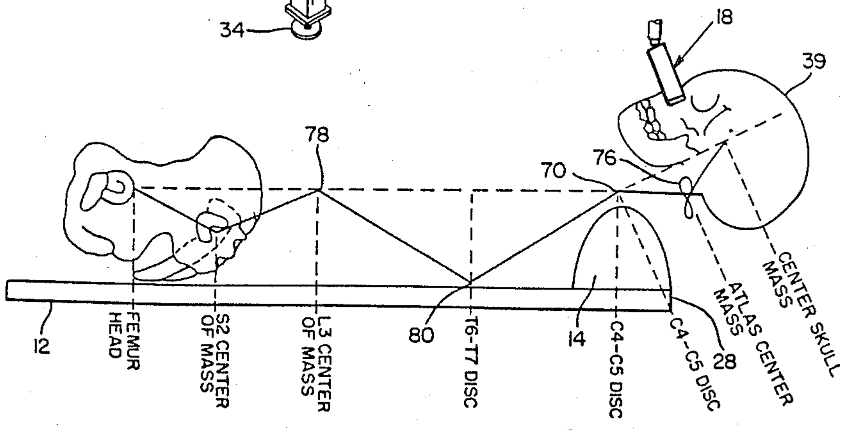
FIG. 4 is a schematic drawing illustrating additional steps in the method of FIG. 3.
Figure 2:
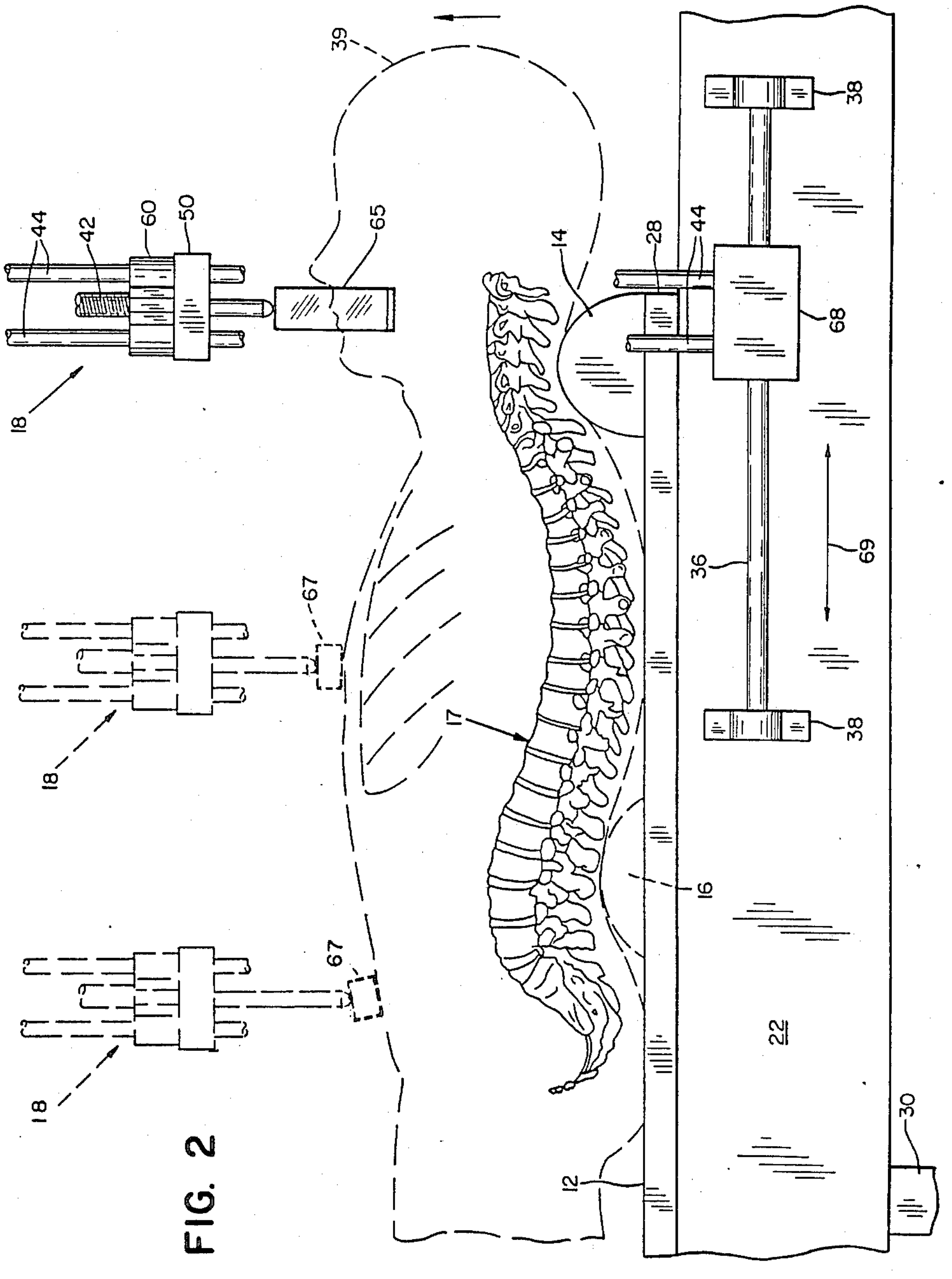
FIG. 2 is a side view of the apparatus of FIG. 1 shown with a person resting thereon.

An apparatus 10 according to the invention is shown is FIGS. 1 and 2. It generally comprises a planar surface 12 with spinal support means such as a cervical support 14 and a lumbar support 16 mounted thereon. Each support 14, 16 has a shape corresponding substantially to its named posterior spinal concavity and is adapted to press against the concavity for aligning its curvature. An oppposing force is applied anteriorly to a spine 17 through a force applicator 18 spaced apart from the planar surface 12. The simultaneous, opposing forces of supports 14, 16 and force applicator 18 are aligned with spine 17 but longitudinally offset relative to each other.

Considering apparatus 10 in more detail, planar surface 12 comprises the top of a supporting table 20. Surface 12 is sized and shaped to support a body supinely thereon and includes a retaining belt 21 for holding the body on table 20. A rectangular frame for supporting surface 12 is comprised on longitudinal beams 22, 23 and transverse beams 24, 25. Longitudinal beams 22, 23 are longer than surface 12 so that a rectangular aperture 26 exists between an inner transverse edge 28 of surface 12 and transverse beam 25. To support table 20, a set of table legs 30 are mounted each within a corner intersection of the beams. Each leg 30 rests on a leveler 34 that can be individually adjusted to level planar surface 12.

Attached to each longitudinal beam 22, 23 is a horizontal guide rod 36 that runs parallel to the beam and is mounted thereto by brackets 38. Horizontal rods 36 support force applicator 18, allowing it to move longitudinally relative to surface 12 and a body thereon. By such movement, force applicator 18 can be positioned to apply a force to the spine through the body opposite either of supports 14, 16. The capability of movement also allows the applicator 18 to be pushed by muscular action of the body as will be described.

Cervical support 14 and lumbar support 16 are removably attached to planar surface 12. Referring to FIG. 2, each support is positioned on surface 12 so that it presses against the associated spinal concavity of a person lying supinely on the planar surface. Support 14 is positioned adjacent to transverse edge 28 to enable the person's skull 39 to tilt backward over edge 28 as force is applied to spine 17 by force applicator 18. The shape of cervical support 14 is generally semicylindrical to correspond to the cervical concavity of spine 17 and includes a groove 29 to receive spine 17. Similarly, the shape of lumbar support 16 is semicylindrical to correspond to the lumbar concavity and includes a corresponding groove 31. Supports 14, 16 are preferably made of a resilient material, such as dense foam rubber, to provide a static pressing force and yet are comfortable to lie upon.

The force on the spine opposing supports 14, 16 is provided by force applicator 18 through a linear actuator 40, such as the type manufactured by Warner Electric Company of South Beloit, Ill. Referring to FIG. 1, actuator 40 includes a body portion 41 from which a piston 42 extends or withdraws under the control of the patient through a control switch 43. Actuator 40 is mounted vertically above table 20 on a moveable frame comprising vertical support rods 44, 46 that straddle surface 12 and crossbars 48, 50 connected to support rods 44, 46. Its body 41 is bolted to upper stationary crossbar 48 within a cover 54 and is retained therein by a cotter pin 56 atop the cover. Piston 42 extends through crossbar 48 and connects at its outer end 58 to lower movable crossbar 50. Vertical blocks 60, 64 at each end of movable crossbar 50 allow it to slide along rods 44, 46 in response to extending or retracting piston 42. On the underside of bar 50 opposite piston 42, a pressure member 66 is pivotally mounted to apply the force anteriorly and normally against the spine through the body. In FIG. 1, member 66 includes a pad 65 for applying force to the skull anteriorly and therethrough to the atlas region of the spine. The same pad 65 or a wider pad 67 can apply force anteriorly to the thoracic region of the spine through the breastbone and to the sacrum region, as shown in FIG. 2.

Force applicator 18 is movably mounted to table 20 so that its force may be applied opposite but offset from either supports 14, 16. As shown in FIG. 1, vertical rods 44, 46 are each attached to a bearing block 68 that rides along horizontal guide rod 36. Force applicator 18 may then be moved longitudinally to position it over the adjacent atlas region of spine 17 when applying force to oppose support 14. Force applicator 18 can also be moved longitudinally of the table to apply force to an adjacent thoracic region of the lumbar vertebrae to oppose support 16 or to the sacrum region. This freedom of movemnt is indicated by arrow 69, shown parallel to rod 36.

Figure 3:
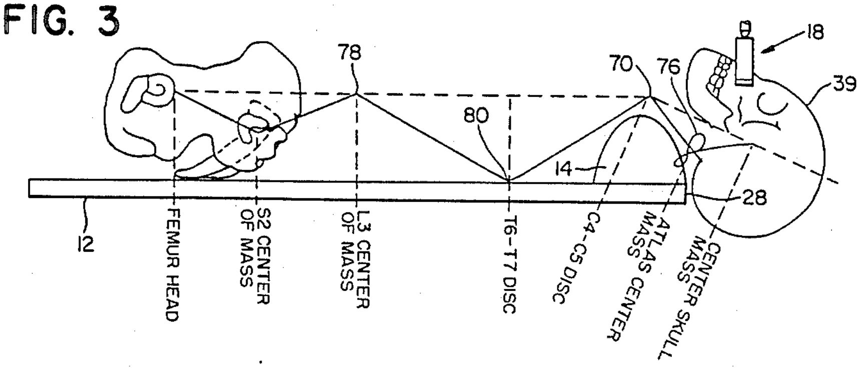
FIG. 3 is a schematic drawing illustrating a method for restoring curvature to the cervical region of the spine.

The method of the invention is illustrated in FIGS. 3 through 6. In FIG. 3, a body rests supinely on a surface 12 with support 14 placed in the cervical concavity underneath cervical vertebrae 70. Support 14 applies a force uniformly to vertebrae 70 to induce correct spinal curvature. A second, opposing force is simultaneously applied by force applicator 18 to the skull 39 through pad 65 which pivots to maintain uniform contact with the skull. The force tilts atlas vertebrae 76 downward over transverse edge 28. This second force is resisted by the patient by raising his skull through muscular action. The skull movement pushes applicator 18 away as the applicator withdraws vertically and slides along guide rods 36 horizontally in response to sufficient pressure. As the applicator 18 is moved, pad 65 continues to pivot to maintain contact with the skull 39.

Figure 5:
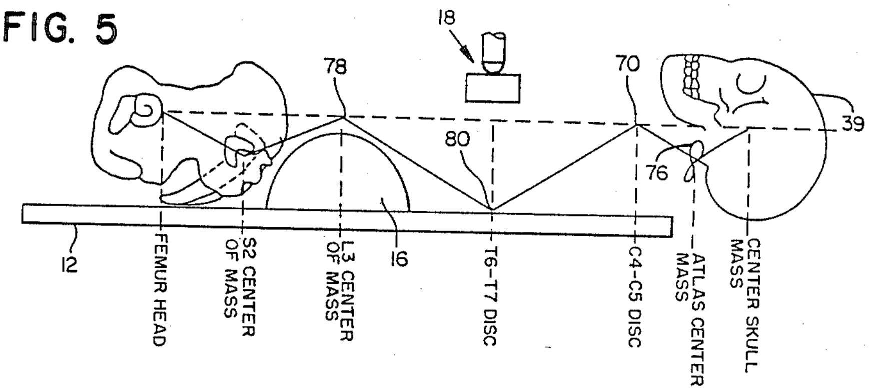
FIG. 5 is a schematic drawing illustrating a method for restoring curvature to the lumbar region of the spine.
Figure 6:
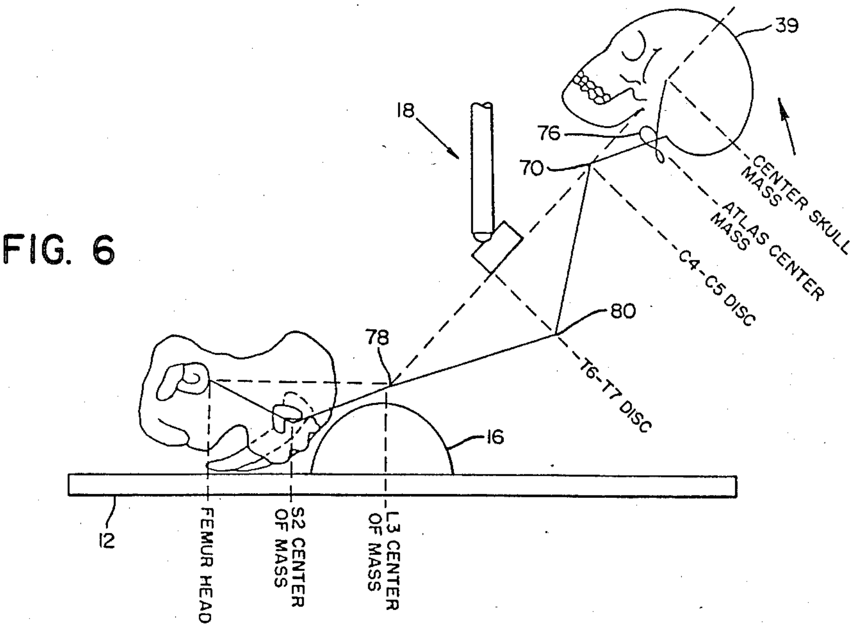
FIG. 6 is a schematic drawing illustrating additional steps in the method of FIG. 5.

The method as applied to the upper lumbar concavity is demonstrated in FIGS. 5 and 6. In FIG. 5, support 16 is placed within the lumbar concavity beneath lumbar vertebrae 78. Support 16 applies a force uniformly to lumbar vertebrae 78 to induce correct spinal curvature as a second, opposing force is applied by means such as force applicator 18 through pad 67. The second force is applied through the breastbone to press downward against the immediate adjacent thoracic vertebrae 80. The patient resists the second force by raising his chest through muscular action. As with the skull, the chest movement pushes applicator 18 vertically and horizontally away as the force of the applicator is withdrawn.

For inducing curvature in the lower lumbar region, the force applicator is initially centered over the sacrum region as shown in dashed lines in FIG. 2, with the lumbar support 16 still in place. The patient resists the second force by raising his hips through muscular action. The hip movement drives the applicator forward toward the head and vertically away from the body as the force is withdrawn in response to sufficient pressure. As in the other instances, the pad 67 pivots to maintain uniform contact with the body during movement.

The method disclosed herein is not limited to the embodiment shown. It may be applied in a horizontal position as described, and it may also be applied with the body at any angle. Furthermore, it is recognized that the method may be improved by applying the second force in a manner such that it remains substantially normal to skull 39 as the skull pivots forward in FIG. 4 and to the breastbone as the body pivots forward in FIG. 6.

Having illustrated and described the principles of the invention in a preferred embodiment, it should be apparent to those skilled in the art that the invention can be modified in arrangement and detail without departing from such principles. I claim all modifications coming within the spirit and scope of the following claims.

I claim:

1. An apparatus for inducing curvature in a human spine, comprising:

a table for supporting the body in an unrestrained position;

spinal support means of a shape corresponding substantially to a concavity of the spine for providing a fulcrum to the unrestrained body to enable portions of the body to extend and flex, the spinal support means being mounted on the table; and a force applicator mounted for longitudinal movement along the table, the applicator having means that extend and press against a portion of the body to be flexed and that will be withdrawn and moved longitudinally of the body as the body flexes in an arc and presses against the applicator whereby the applicator resists yet accommodates both the longitudinal and perpendicular components of the arcuate path of the flexing body.

2. The apparatus of claim 1 in which the force applicator includes means for controlling its operation by a patient of the table.

3. The apparatus of claim 1 in which the table includes a transverse edge over which a patient's skull can be placed and a cervical support mounted adjacent the transverse edge for providing the fulcrum to enable the force applicator means to apply force against the skull to move the atlas region of the spine.

4. The apparatus of claim 1 in which the spinal support means comprises a lumbar support of a shape corresponding substantially to the posterior concavity of the lumbar region of the spine and the force applicator means is adapted to apply force anteriorly to an adjacent thoracic region of the spine.

5. The apparatus of claim 1 in which the spinal support means comprises a cervical support of a shape corresponding substantially to the posterior concavity of the cervical region of the spine and the force applicator means is adapted to apply force anteriorly to an adjacent atlas region of the spine.

6. The apparatus of claim 1 in which the force applicator comprises an actuator having a piston that extends against the body and withdraws from the body, the actuator providing the force against which the body is pressed.

7. The apparatus of claim 1 which the force applicator includes an end portion pivotally connected to the applicator for applying its force normally to the flexed portion of the body.

8. A method for inducing curvature in a human spine within the body, comprising:

providing means applying a first force uniformly to the inside of a spinal concavity in which curvature is to be induced to provide a therefor;

providing means applying a second force simultaneously to the opposite side of the spinal concavity at the end of the concavity, the second force being offset from the first force;

providing means flexing the body in an arc from the fulcrum and pressing the body against the second force; and withdrawing the second force both longitudinally of the body and perpendicularly thereto in response to the body force as the body is flexed, whereby the second force continues to press against the body as the body forces the second force providing means essentially in the arc of body movement.

* * * * *

UNITED STATES PATENT AND TRADEMARK OFFICE
CERTIFICATE OF CORRECTION

PATENT NO. : 4,686,968

DATED : August 18, 1987

INVENTOR(S) : John S. Scherger

It is certified that error appears in the above-identified patent and that said Letters Patent is hereby corrected as shown below:

Column 6, line 46, after "to provide a" insert --fulcrum--.

Signed and Sealed this

Twenty-second Day of March, 1988

Attest:

DONALD J. QUIGG

*Attesting Officer*

*Commissioner of Patents and Trademarks*